United States Patent [19]
Wakisaka et al.

[11] Patent Number: 4,713,241
[45] Date of Patent: Dec. 15, 1987

[54] BACTERIAL INSECTICIDE AND PRODUCTION THEREOF

[75] Inventors: Yoshiharu Wakisaka, Hyogo; Junko Uo, Kyoto; Kouichi Matsumoto, Osaka; Osamu Ohodaira, Osaka; Kentaro Tanaka, Osaka, all of Japan

[73] Assignee: Shionogi & Co., Ltd., Osaka, Japan

[21] Appl. No.: 661,178

[22] Filed: Oct. 15, 1984

Related U.S. Application Data

[62] Division of Ser. No. 349,256, Feb. 16, 1982, abandoned.

[30] Foreign Application Priority Data

Feb. 27, 1981 [JP] Japan .................. 56-28781

[51] Int. Cl.$^4$ ............... A01N 63/00; C12N 1/20; C12P 21/00; C12R 1/07
[52] U.S. Cl. ............................ 424/93; 435/68; 435/253; 435/832
[58] Field of Search ............ 435/253, 240, 832, 172.1, 435/68; 424/93

[56] References Cited

U.S. PATENT DOCUMENTS 4,277,564  7/1981  Johnson .................. 435/253
4,609,550  9/1986  Fitz-James .............. 424/93

FOREIGN PATENT DOCUMENTS 268796  9/1968  U.S.S.R. .................. 424/93

OTHER PUBLICATIONS

Yousten, 1978, "A Method for the Isolation of Asporogenic Mutants of *Bacillus thuringiensis*", Can. J. Micro., v 24, pp. 492–494.

Primary Examiner—Thomas G. Wiseman
Assistant Examiner—Karen Maurey
Attorney, Agent, or Firm—Wenderoth, Lind & Ponack

[57] ABSTRACT

A bacterial insecticide containing an insecticidal substance produced by a practically reversionless asporogenous mutant of *Bacillus thuringiensis*, especially *Bacillus thuringiensis* serovar. *kurstaki* 290-1 and the process for the production in addition to a practically reversionless asporogenous mutant of *Bacillus thuringiensis*, especially *Bacillus thuringiensis* serovar. *kurstaki* 290-1 and the process for the production.

6 Claims, No Drawings

BACTERIAL INSECTICIDE AND PRODUCTION THEREOF

This application is a division of application Ser. No. 349,256, filed Feb. 16, 1982, now abandoned.

This invention relates to an insecticide containing an insecticidal substance produced by a practically reversionless asporogenous mutant of *Bacillus thuringiensis* and production thereof. Furthermore, it relates to a practically reversionless asporogenous mutant or *Bacillus thuringiensis* and the process for the production.

Chemical insecticides generally used have many disadvantages in, for example, having adverse influence on men, beasts and fishes, toxic residue, induction of drug-resistant insects and the like. Many research and development programs have been carried out to find an alternative insecticide. Research for bacterial agricultural chemicals utilizing *Bacillus thuringiensis* has been conducted as a link in the chain of the programs and the research has been partly put to practical use. It is based on utilization of insecticidal activity of δ-endotoxin (abbreviated to as δ-toxin hereinafter). In general, *Bacillus thuringiensis* produces crystals of δ-toxin and spores in the cells. The crystals and spores are usually released out of the cells when cell walls naturally rip at the final stage of cultivation and strengthen activity available as insecticide. The whole culture broth is usually dried and applied directly without separating the crystals from the spores when *Bacillus thuringiensis* is used as an insecticide because the separation procedure is very complicated. Unfortunately, however, the application is extremely restricted since there is the possibility that the spores in the preparation will be multiplied in the natural world after application and cause hazzard on the sericulture. The creation of an asporogenous strain of *Bacillus thuringiensis* was attempted to remove the defect and an insecticide containing *Bacillus thuringiensis* but not causing secondary contamination to silkworms was developed (Japan. Pat. Pub. (unexamined) No. 50/125022).

The inventors of this invention, however observed in their investigation that 1–10 or more spores/ml were present in a fermented broth of *Bacillus thringiensis* asporogenous mutant discovered by the present inventors. The spores are likely to be derived from reverse mutation of the mutant. The same reverse mutation is confirmed in all reported asporogenous mutants.

The inventors, thereupon, aimed to create a completely reversionless asporogenous mutant which had completely lost sporulation and renaturation abilities and develop an insecticide giving no adverse secondary contamination to silkworms, i.e. no secondary multiplication. As the result, a practically reversionless asporogenous mutant was obtained by mutation with ethyl methanesulfonate. The inventors have completed this invention by confirming that the fermented broth of the mutant does not contain any detectable spore and is obviously utilizable as safe insecticidal substance. Thus, a reversionless asporogenous mutant was created by the present inventors for the first time. This invention provides a novel and useful bacterial insecticide using the said mutant and the process for the production in addition to a novel practically reversionless asporogenous mutant and the process for the production.

The above practically reversionless asporogenous mutant can be obtained by treating the spore of an asporogenous mutant with a mutagen inducing deletion mutation, e.g. alkyl alkanesulfonate, especially ethyl methanesulfonate. The parent strains to be used are asporogenous mutants of *Bacillus thuringiensis*, e.g. *Bacillus thuringiensis* serovar. *kurstaki*, *aizawai*, *thuringiensis*, *alesti*, *galleriae*, *tolworthi*, *subtoxicus* and the like; *kurstaki* being preferred. The asporogenous mutants are disclosed in Japan. Pat. Pub. (unexamined) No. 50/125022, J. Invertebr. Pathol. 25, 355–361 (1975), Eur. J. Biochem. 18, 226–239 (1971) and Can. J. Microbiol. 24, 492–494 (1978). An example for preparing a practically reversionless asporogenous mutant is shown below.

EXPERIMENT 1

A suspension of spores of *Bacillus thuringiensis* serovar, *kurstaki* IK (10 ml, ca. $10^8$ spores/ml, 0.1M phosphate buffer solution, pH 7.0) was heated at 70° C. for 15 minutes. After cooling to room temperature, ethyl methanesulfonate[1] (0.25 ml) was added thereto. The mixture was shaken at 28° C. for 15–18 hours and centrifuged under aseptic conditions ($\times 4000$, 20 minutes, 5° C.). The precipitate was washed with a sterile saline solution by centrifugation two times and then suspended in 0.1M sterile phosphate buffer solution (pH 7.0, 5.0 ml). The suspension was used to rub the surface of 30 Petri dishes into which CL-agar medium[2] (15 ml) had been poured in the proportion of 100 μl of the suspension to a Petri dish. After incubation at 28° C. for 2–5 days, the resultant colonies were isolated about 200–300 per lot by random isolation method.

The isolated colonies were inoculated on a nutrient agar disks and after incubation at 28° C. for 3–5 days the presence of spore and δ-toxin was checked. On the other hand, the colonies were incubated on CL-agar disks, incubated at 28° C. for 1 day and then kept at 5° C.

In the above test, 42 colonies did not form any detectable spore and had good productivity to δ-toxin. They were incubated on both 10 ml of M medium[3] and S medium[4] and incubated at 28° C. for 3–4 days under shaking. About 5 ml each of incubated media were heated at 70° C. for 20 minutes and number of spores per 1 ml were counted. The rest of the heated media was centrifuged, washed with water and lyophilized. Insecticidal activity of the thus-obtained cell to silkworms was measured. Besides, the steadiness of δ-toxin production by the test strains was also observed.

Four strains were selected owing to their nature, i.e. no formation of spore, abundant production of δ-toxin and stability. The strains were inoculated on S medium (100 ml) in Sakaguchi flasks and incubated at 28° C. for 3–4 days. Incubation was repeated from 7 to 17 times and number of spores and producibility of δ-toxin per 5 ml of medium were measured. As the result, strain 290–1 was obtained, of which the spore formation was not observed during the incubation over 17 generations.

Notes:
(1). Ito, J. and J. Spizizen: Radiation Research 13, 93–96 (1971)
(2). CL-agar medium: 0.25% glycerol, 0.5% polypeptone, 0.5% casein, 0.3% sodium chloride, 1.25% agar.
(3). M medium: 0.5% glucose, 1.0% polypeptone, 0.5% lactocasein, 1.0% cane molasses, 0.3% sodium chloride.
(4). S medium: 3.0% starch, 3.0% soybean meal, 1.5% corn steep liquor, 0.1% sodium carbonate, 0.3% ammonium sulfate.

The above strain 290-1 was named *Bacillus thuringiensis* var. *kurstaki* 290-1 and has been deposited in Agency of Industrial Science & Technology, Fermentation Research Institute and 1—1, Higashi 1-cho, Yatabemachi, Tsukuba-gun, Ibaraki Pref. Japan under FERM-P No. 5794 since Dec. 3, 1980. The strain also has been deposited in American Type Culture Collection in 12301, Parklawn Drive, Rockville, Md., U.S.A. under accession number 31813 since Feb. 25, 1981. Besides, the name is correctly revised to *Bacillus thuringiensis* serovar. *kurstaki* 290-1 in this specification according to rule of nomenclature.

The parent strain of strain 290-1 was isolated in a test field of Shionogi & Co., Ltd. in Japan and identified to be the same as a strain HD-1 being recognized as *Bacillus thuringiensis* serovar. *kurstaki* from the description in J. Invertebr. Pathol. 11, 335-347 (1968), ibid. 15, 139-140 (1970), ibid. 15, 232-239 (1970) and ibid 22, 273-277 (1973).

Strain 290-1 has the same properties as the parent strain except for the irreversibility of spore formation. Strain 290-1 produces almost the same amount of δ-toxin as the parent strain and does not form any spore even in 17 times of subinoculations. Additionally, no spore was detected neither in 30.5 ml of S medium after 3 days incubation nor 45 ml of M medium after the same incubation period. The results of irreversibility test of strain 290-1 are shown below.

EXPERIMENT 2

Strain 290-1 was inoculated on S medium (100 ml) in a Sakaguchi flask and incubation at 28° C. for 4 days was repeated 17 times. The fermented media of each time were heated at 70° C. for 15 minutes and transferred to a nutrient agar medium. After incubation at 28° C. for 3-4 days, formation of spore was checked. Simultaneously, insecticidal activity was measured with lyophilizate of precipitate of centrifugation. The assay for measuring the activity has been disclosed by Nishiitsutsuji-Uwo et al. in J. Invertebr. Pathol. 29, 162-169 (1977). The result is shown in Table 1.

TABLE 1

| Incubation Frequency | 1 | 2 | 3 | 4 | 5 | 6 |
|---|---|---|---|---|---|---|
| Number of Spore/ Number of Petri dish | 0/1 | 0/5 | 0/5 | 0/5 | 0/5 | 0/2 |
| Relative Activity/ml | 874 | 1036 | 645 | 1065 | 870 | 2152 |
| Incubation Frequency | 7 | 8 | 9 | 10 | 11 | 12 |
| Number of Spore/ Number of Petri dish | 0/2 | 0/2 | 0/2 | 0/2 | 0/2 | 0/3 |
| Relative Activity/ml | 1122 | 999 | 2088 | 2034 | 1533 | 733 |
| Incubation Frequency | 13 | 14 | 15 | 16 | 17 | |
| Number of Spore/ Number of Petri dish | 0/3 | 0/3 | 0/3 | 0/3 | 0/3 | |
| Relative Activity/ml | 647 | 508 | 1357 | 1164 | 1067 | |

EXPERIMENT 3

The broth of strain 290-1 preliminarily incubated on a CL-agar medium at 28° C. for 1 day was inoculated on a nutrient broth and incubated at 28° C. for 1 day under shaking. The fermented broth was inoculated on an M medium (60 ml) and an S medium each in a 300 ml Erlenmeyer flask at the final concentration 2% and incubated at 28° C. for 3 days. Both 15 ml of the fermented media were transfered into non-necked test tubes with caution not to touch the wall and heated at 70° C. for 30 minutes. The fermented M medium was portioned into 1 ml each on 5 Petri dishes, 1.5 ml each on 20 Petri dishes and 2.0 ml each on 5 Petri dishes respectively. The fermented S medium was portioned into 0.5 ml each on 11 Petri dishes and 1.0 ml each on 25 Petri dishes respectively. All dishes were incubated at 28° C. for 2.4 days and no formation of colony was observed.

Accordingly, it was confirmed that spore was not formed in 45 ml of fermented M medium nor in 30.5 ml of fermented S medium. The result of the test was converted into as the ratio to number of living cells and cell weight, which are shown in Table 2: In the same manner, a practically reversionless asporogenous mutant can be obtained from other varieties by the usual method.

TABLE 2

| | M medium | S medium |
|---|---|---|
| Number of Spore/ Number of Living Cell | $0/2.1 \times 10^{10}$ | $0/5.1 \times 10^{9}$ |
| Number of Spore/ Cell Weight | 0/90 mg | 0/549 mg |

As shown above, the reversionless asporogenous mutant prepared by this inventors does not form any spore practically. Thus, the fermented broth is utilized as insecticide in itself. Besides, "insecticidal substance" of this invention includes not only the free crystalline δ-toxin above mentioned but also the living cells of practically reversionless asporogenous mutant of *Bacillus thuringiensis*, especially *Bacillus thuringiensis* serovar. *kurstaki* 290-1, containing the above crystals, the dead cells and the mixture, fermented broth containing bacteria cells and/or the free crystals, condensate of the fermented broth, their dried correspondents and the like.

The production of the insecticidal substance of the above practically reversionless asporogenous strain follows the methods of producing the insecticidal substance of the parent strain. The insecticidal substance can also be produced by the method disclosed in Japan. Pat. Pub. (unexamined) No. 50/125022 and the method by Dulmage, H. T. in J. Invertebr. Pathol. 22, 237-277 (1971). More practically, a practically reversionless asporogenous mutant of *Bacillus thuringiensis*, especially *Bacillus thuringiensis* serovar. *kurstaki* 290-1 is inoculated on an organic medium being abundant in nitrogen sources and carbon sources. The yield of δ-toxin is remarkably increased when the medium contains potassium ion at the final concentration being about 2-50 mM, more favorably 3-30 mM. Additionally, production of δ-toxin is largely affected by aeration volume, especially oxygen supply. The fermentation under sufficient oxygen supply brings about rich production of δ-toxin. Fermentation may be continued at about 25°-30° C. for about 2-5 days under heavy aerobic condition. There are exemplified sucrose, maltose, glucose, fructose, can molasses, beet sugar, corn steep liquor and the like as carbon sources. Nitrogen sources are, for example, ammonium sulfate, ammonium chloride, cotton seed powder, soybean meal, casein hydrolysate and the like. Minerals and vitamins may be added, if necessary. Fermentation is effected under aerobic condition as noted above. Submerged aeration fermentation is preferred in a large scale production.

After fermentation is completed, generally used methods such as centrifugation, filtration and the like may be applied in the case that it is preferred to isolate insecticidal substance such as free δ-toxin crystals, cells and the like. It is also appropriate to apply ordinary concentration and drying methods in order to pulverize the fermented broth containing cells and/or free crystals. Practically, spray-drying method popularly used in these days can be preferrably be applied because fine powder can be obtained without decrease of activity. In the method wettable powder can be obtained at one operation by adding a fixing agent, a spreader, a diluent and the like to a cell floating liquid at spray-drying. Ordinary sterilizing method can be used, if necessary, when the product obtained by the above methods contains living cells. There are exempified heating, supersonic treatment, irradiation with X ray and the like as physical sterilization, treatment with formalin, hydrogen peroxide, sulfites, nitrofurylacrylamide, furylfuramide, chlorine compounds, β-propiolactone, nitrites, nitrates, surfactants, ethylene oxide, propylene oxide and the like as chemical sterilization and autolysis, treatment with phage, treatment with lysozyme as biological sterilization. Heating and chemical sterilization are convenient for industrial scale production among the above sterilization methods. Spray-drying method is particularly useful for pharmaceutical preparation in no necessity of sterilization process since the product is simultaneously heated.

Thus obtained insecticidal substance is formulated into pharmaceutical preparations, for example, tablets, granules, powders, wettable powders, suspensions, emulsions, pastes and the like. There is added filler, for example, kaolin, bentonite, talc, diatomaceous earth, wheat meal and sugars, with spreaders, sufactants, stabilizers and the like during the preparation procedure, if necessary. Other insecticides, sterilizers, herbicides, plant growth regulatores, flavours, nitrients, and the like may be added, if desired, as long as it does not give adverse influence on the insecticidal activity.

The insecticide obtained by this invention is effective against laravae of Lepidoptera such as *Plutella maculipennis* Curtis, *Chilo suppressalis* Walker, *Cnidocampa flavescens* Walker, *Pieris rapae crucivora* Boisduval, *Momestra brassicae* Linne, *Papilio machaon hippocrates* Felder et Felder, *Chalcosia remota* Walker, *Stauropos fagi persimilis* Butler, *Arctia caja* Linne, *Pernara guttata* Bremer et Grey and the like. The insecticide can be sprayed freely to rice fields, fields, forests and waste lands without regard for the hazzard to silkworms because it does not cause the secondary multiplication.

The invention is exemplified more in detail in the following examples.

EXAMPLE 1

KB-5 medium: 1.0% potato starch, 0.5% glucose, 1.5% soybean meal, 2.0% Pharmamedia ®, 1.0% powdery pork meat, 0.2%, polypeptone, 0.03% magnesium sulfate heptahydrate, 1.0% calcium carbonate, 0.002% zinc sulfate heptahydrate, and 0.002% ferrous chloride.

*Bacillus thuringiensis* serovar. *kurstaki* 290-1 (FERM-P No. 5794) was cultured on a nitrient agar medium at 28° C. for one day, and one platinum-loopful of the resultant broth was inoculated on a nutrient medium (700 ml) in a 2 L Meyer flask, and cultured with shaking (180 r.p.m.) at 28° C. for 12 hours. The resultant culture broth was inoculated on a KB-5 medium (15 L) of the above mentioned composition in a 30 L jar, and after culturing under aeration and agitation (400 r.p.m.) at 28° C. for 52 hours, the fermented broth was treated by sharples centrifugation ($\times$13,000 g) to give 15.2 mg/ml (dry weight) of insecticidal material (activity: 3070/ml). The activity is measured by the method as described in J. Invertebr. Pathol. 29, 162-169 (1977) (Nishiitsutsuji-Uwo, J., et al.).

EXAMPLE 2

The culture was carried out in the same manner as in Example 1 employing the S medium (its composition is mentioned above) instead of the KB-5 medium for fermentation to give 14.7 mg/ml (dry weight) of insecticidal material (activity: 2279/ml).

EXAMPLE 3

The cells of bacterium obtained in Example 2 (the insoluble precipitate after centrifugation) were suspended in water so that the concentration of the insoluble component was about 5% w/v. The resultant suspension was spray-dried with Minispray (made by Yamato Scientific Co. Ltd., model DL-21). Minispray is maintained under the following conditions: inlet temperature: 190° C.; outlet temperature: 90° C. or lower; flow rate of solution: 3-4 ml/min.; flow rate of hot air: 0.4-0.5 m$^3$/min.; spraying pressure at the binary nozzle: 3.0-1.0 Kg/cm$^2$; air rate at the nozzle: 13-9 L/min.

The activity and particle size of the resultant powder specimen are shown in Table 3 in comparison with the result of a powder specimen prepared by lyophilization of a part of the above suspension followed by pulverization with a fluid energy mill (alias jet mill). Powder specimens prepared by the above two methods respectively are almost equal in activity and particle size.

TABLE 3

| | The Spray-Drying Method | | | | | The Jet Mill Method[1] |
|---|---|---|---|---|---|---|
| A. Binary Nozzle | | | | | | |
| Spraying Pressure kg/cm$^2$ | 3.0 | 2.5 | 2.0 | 1.5 | 1.0 | |
| Air Rate L/min. | 13 | 13 | 11 | 11 | 9 | |
| B. Dried Powder | | | | | | |
| Moisture % | 8.7 | 7.3 | 6.9 | 4.9 | 6.2 | 5.5 |
| LC$_{50}$[2] μg/ml | 87 | 59 | 66 | 71 | 71 | 58 |
| Particle Size (R) %[3] | | | | | | |
| >10μ | 8.6 | 8.8 | 6.9 | 8.4 | 8.9 | 6.0 |
| >4μ | 13.5 | 14.0 | 12.5 | 14.4 | 13.9 | 12.0 |
| >2μ | 25.6 | 26.3 | 23.8 | 28.0 | 26.8 | 24.7 |
| >1.5μ | 39.7 | 40.0 | 35.0 | 43.3 | 39.7 | 33.7 |
| >1.2μ | 53.7 | 52.5 | 49.0 | 56.3 | 54.3 | 49.5 |
| >1.0μ | 64.2 | 64.0 | 60.7 | 66.2 | 65.8 | 54.7 |
| >0.8μ | 75.2 | 75.3 | 73.2 | 76.8 | 76.4 | 66.4 |
| >0.6μ | 85.5 | 85.4 | 84.0 | 86.5 | 85.3 | 79.0 |

Note:
[1]The lyophilizate contained 2.7% moisture and the activity was LC$_{50}$ 67 μg/ml.
[2]LC$_{50}$ shows 50% lethal concentration (μg/ml) for silkworms.
[3]Particle size was measured with an apparatus (CP-50; Shimazu Co., Ltd.) of phototransmission type for measuring particle size distribution on the basis of centrifugal sedimentation.

EXAMPLE 4

In the same manner as in Example 2, the culture was made under aeration and agitation on the S medium for 54 hours to give insecticidal material specimen. And the resultant insecticidal specimen was suspended in water so that the concentration of the insoluble solid component was about 3%. The additives as shown in Table corresponding to one third amount of the insoluble solid component were added to the suspension and spray-dried. Calculated value of LC$_{50}$ in this case is 86.

The activity of the obtained specimens and the effect of sterilization are shown in Table 4.

TABLE 4

| Sample No. | Additive | LC$_{50}$ μg/ml | Number of live bacteria/mg |
|---|---|---|---|
| 1 | Non | 53 | 0 |
| 2 | Non | 45 | 0 |
| 3 | Gum arabic powder | 62 | 0 |
| 4 | Methyl cellulose (500 cps) | 57 | 0 |
| 5 | Polyvinylalcohol | 75 | 0 |
| 6 | Carboxymethyl cellulose | 78 | 0 |
| 7 | Hydroxypropylmethyl cellulose phthalate (pH 5.0) | 84 | 0 |
| 8 | New Cargen NX 405H* | 72 | 0 |
| 9 | Talc | 70 | 0 |
|   | Lyophilized specimen | 65 | — |

*Made by Takemoto oil & fat Co. Ltd.

EXAMPLE 5

Powdery preparation prepared by combination of spray-dry powder (25 parts) from *Bacillus thuringiensis* var. *kurstaki* 290-1 obtained in Example 3 with talc (75 parts). The preparation may be used in an amount of 100 g or more per 10 are.

EXAMPLE 6

Spray-dry powder (25 parts) obtained in Example 3, sodium dodecylbenzenesulfonate (2 parts), sodium dinaphthylmethanedisulfonate (2 parts) and a mixture (71 parts) of kieselguhr and clay are mixed and pulverized to give wettable powder.

EXAMPLE 7

Powdery preparation prepared by combination of the powder (30 parts) obtained by spray-drying together with carboxymethyl cellulose in Example 4 with talc (70 parts).

What we claim is:

1. A condensate or dried bacterial insecticidal substance produced by fermentation of *Bacillus thuringiensis* serovar. *kurstaki* 290-1 (ATCC 31813), in an organic culture medium therefor containing carbon and nitrogen sources at about 25° to 30° C. for about 2 to 5 days under highly aerobic conditions, said insecticidal substance being selected from the group consisting of (a) living cells of said microorganism containing crystalline δ-toxin, (b) dead cells of said microorganism containing said crystalline, δ-toxin, and (c) mixtures thereof.

2. A bacterial insecticidal substance according to claim 1 which comprises dried material obtained by spray drying fermented broth produced by fermentation of *Bacillus thuringiensis* serovar. *kurstaki* 290-1 (ATCC 31813), in an organic culture medium therefor containing carbon and nitrogen sources at about 25° to 30° C. for about 2 to 5 days under highly aerobic conditions.

3. A process for preparing a bacterial insecticidal substance which comprises cultivating *Bacillus thuringiensis* serovar. *kurstaki* 290-1 (ATCC 31813) in an organic culture medium therefor containing carbon and nitrogen sources at about 25°-30° C. for about 2-5 days under highly aerobic condition, collecting the insecticidal substance and subjecting the insecticidal substance to spray-drying.

4. A process as claimed in claim 3 wherein the cultivation is effected in the presence of a potassium ion at a concentration of 2-50 mM.

5. A process as claimed in claim 3 wherein the cultivation is effected in the presence of a potassium ion at a concentration of 3-30 mM.

6. A practically reversionless asporogenous mutant *Bacillus thuringiensis* serovar. *kurstaki* 290-1.

* * * * *